United States Patent
Tian et al.

(10) Patent No.: US 10,919,978 B2
(45) Date of Patent: Feb. 16, 2021

(54) ANTIBODY OR ANTIBODY FRAGMENT CAPABLE OF BINDING TO LUNG-SPECIFIC X PROTEIN AND USE THEREOF

(71) Applicant: Immunopharmaceutic Institute of Hefei Ruida Co., Ltd., Hefei (CN)

(72) Inventors: Zhigang Tian, Hefei (CN); Haiming Wei, Hefei (CN); Xiaohu Zheng, Hefei (CN); Rui Sun, Hefei (CN); Weihua Xiao, Hefei (CN); Dan Liu, Hefei (CN); Baoru Wang, Hefei (CN)

(73) Assignee: IMMUNOPHARMACEUTIC INSTITUTE OF HEFEI RUIDA CO., LTD., Hefei (CN)

( * ) Notice: Subject to any disclaimer, the term of this patent is extended or adjusted under 35 U.S.C. 154(b) by 157 days.

(21) Appl. No.: 16/302,883

(22) PCT Filed: May 25, 2017

(86) PCT No.: PCT/CN2017/085836
§ 371 (c)(1),
(2) Date: Nov. 19, 2018

(87) PCT Pub. No.: WO2018/126595
PCT Pub. Date: Jul. 12, 2018

(65) Prior Publication Data
US 2019/0322758 A1 Oct. 24, 2019

(30) Foreign Application Priority Data

Jan. 4, 2017 (CN) .......................... 201710004133.X

(51) Int. Cl.
| | |
|---|---|
| A61P 35/00 | (2006.01) |
| C07K 16/18 | (2006.01) |
| C07K 16/30 | (2006.01) |
| G01N 33/574 | (2006.01) |
| A61K 39/00 | (2006.01) |

(52) U.S. Cl.
CPC .......... *C07K 16/3023* (2013.01); *A61P 35/00* (2018.01); *C07K 16/18* (2013.01); *G01N 33/57423* (2013.01); *A61K 2039/505* (2013.01); *C07K 2317/24* (2013.01); *C07K 2317/732* (2013.01)

(58) Field of Classification Search
CPC ..... C07K 16/3023; C07K 16/18; A61P 35/00; G01N 33/57423
USPC ..................................................... 424/133.1
See application file for complete search history.

(56) References Cited

FOREIGN PATENT DOCUMENTS

| CN | 1772925 A | 5/2006 |
|---|---|---|
| CN | 103012587 A | 4/2013 |
| JP | 2001078772 A | 3/2001 |

OTHER PUBLICATIONS

Zheng, Xiaohu et al., "Targeting LUNX Inhibits Non-Small Cell Lung Cancer Growth and Metastasis", Cancer Res. Mar. 15, 2015;75(6):1080-90. doi: 10.1158/0008-5472.CAN-14-1831. Epub Jan. 19, 2015.

Bingle, Lynne et al., "SPLUNC1 (PLUNC) Is Expressed in Glandular Tissues of the Respiratory Tract and in Lung Tumours With a Glandular Phenotype", Journal of Pathology, 2005, pp. 491-497; www.interscience.wiley.com doi: 10.1002/path.1726.

Chothia, Cyrus and Arthur M. Lesk, "Canonical Structures for the Hypervariable Regions of Immunoglobulins", J. Mol. Biol. (1987) 196, 001-017.

Fazekas de St. Groth, S. and Doris Scheidegger, "Production of Monoclonal Antibodies: Strategy and Tactics", Journal of Immunological Methods, 35 (1980) 1-21.

Kohler, G. and C. Milstein, "Derivaton of Specific Antibody-Producing Tissue Culture and Tumor Lines By Cell Fusion", Eur. J. Immunol. 1976, 6:511-519.

Mechetner, E. (2007) "Development and Characterization of Mouse Hybridomas" in Albitar, Maher (Ed.), Monoclonal Antibodies: Methods and Protocols, Methods in Molecular Biology 378, Totowa, New Jersey: Humana Press, pp. 1-13.

Gefter, Malcolm L. et al., "A Simple Method for Polyethylene Glycol-Promoted Hybridization of Mouse Myeloma Cells", Somatic Cell Genetics, vol. 3, No. 2, 1977, pp. 231-236.

Larrick, J.W. et al., "Immunoglobulin V Regions of a Bactericidal Anti- Neisseria meningitidis Outer Membrane Protein Monoclonal Antibody", Scand. J. Immunol. 32, 121-128, 1990.

Li, Jian et al., "LUNX mRNA-positive Cells At Different Time Points Predict Prognosis in Patients With Surgically Resected Nonsmall Cell Lung Cancer", 2014 Mosby, Inc., http://dx.doi.org/10.1016/j.trsl.2013.09.010.

Zheng, Xiaohu (2015), "The antitumor effects of LunX and EpCAM antibody" (Doctoral dissertation), University of Science and Technology of China.

(Continued)

Primary Examiner — Yan Xiao
(74) Attorney, Agent, or Firm — Volpe Koenig

(57) ABSTRACT

The present application provides an antibody or antibody fragment capable of binding to a lung-specific X protein and being used to treat a tumor, and a use thereof. The antibody or antibody fragment includes heavy chain CDRs having amino acid sequences of SEQ ID NO: 1, SEQ ID NO: 2, and SEQ ID NO: 3 and light chain CDRs having amino acid sequences of SEQ ID NO: 4, SEQ ID NO: 5, and SEQ ID NO: 6. Alternatively, the antibody or antibody fragment includes heavy chain CDRs having amino acid sequences of SEQ ID NO: 1, SEQ ID NO: 7, and SEQ ID NO: 3 and light chain CDRs having amino acid sequences of SEQ ID NO: 8, SEQ ID NO: 5, and SEQ ID NO: 6. The antibody is a chimeric antibody.

8 Claims, 2 Drawing Sheets

Specification includes a Sequence Listing.

(56) References Cited

OTHER PUBLICATIONS

Zheng, Xiaohu (2014) "Novel Biotherapy Target-Lunx Protein for Lung Cancer", Proceedings of the Ninth Congress of the Chinese Society for Immunology.
Mitas, Michael et al. "LUNX Is A Superior Molecular Marker for Detection of Non-Small Lung Cell Cancer in Peripheral Blood", Journal of Molecular Diagnostics, vol. 5, No. 4, Nov. 2003.
Kabat et al., Sequences of Proteins of Immunological Interest, 5th Ed. Public Health Service, National Institutes of Health, Bethesda, MD. (1991) and Coloma, J. J. et al., (1991) BioTechniques, 11, 152-156.
Tobinai Masato Kensei Tobinai A Molecular Target Therapeutic Molecular for Non-Hodgkinin Lymphomas, a Separate Volume, a Medicine for Medical Purposes, and a Separate Volume or Medical Targeting Therapy of Non-Hodgkin Lymphoma Blood-diseases—State of Arts Ver.3, 2005.

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial
<220> FEATURE:
<223> OTHER INFORMATION: The sequence is synthesized

<400> SEQUENCE: 1

Arg Ser Trp Met Ser
1               5

<210> SEQ ID NO 2
<211> LENGTH: 17
<212> TYPE: PRT
<213> ORGANISM: Artificial
<220> FEATURE:
<223> OTHER INFORMATION: The sequence is synthesized

<400> SEQUENCE: 2

Arg Ile Tyr Pro Gly Asp Gly Asp Thr Lys Tyr Ser Gly Lys Phe Glu
1               5                   10                  15

Gly

<210> SEQ ID NO 3
<211> LENGTH: 11
<212> TYPE: PRT
<213> ORGANISM: Artificial
<220> FEATURE:
<223> OTHER INFORMATION: The sequence is synthesized

<400> SEQUENCE: 3

Ser Gly Gly Ile Gln Gly Tyr Gly Met Asp Tyr
1               5                   10

<210> SEQ ID NO 4
<211> LENGTH: 15
<212> TYPE: PRT
<213> ORGANISM: Artificial
<220> FEATURE:
<223> OTHER INFORMATION: The sequence is synthesized

<400> SEQUENCE: 4

Arg Ala Ser Lys Ser Val Ser Thr Ser Gly Tyr Thr Tyr Met His
1               5                   10                  15

<210> SEQ ID NO 5
<211> LENGTH: 7
<212> TYPE: PRT
<213> ORGANISM: Artificial
```

<220> FEATURE:
<223> OTHER INFORMATION: The sequence is synthesized

<400> SEQUENCE: 5

Leu Ala Ser Lys Leu Glu Ser
1               5

<210> SEQ ID NO 6
<211> LENGTH: 7
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (5)..(5)
<223> OTHER INFORMATION: Xaa is D or E

<400> SEQUENCE: 6

Gln His Ser Arg Xaa Leu Thr
1               5

<210> SEQ ID NO 7
<211> LENGTH: 17
<212> TYPE: PRT
<213> ORGANISM: Artificial
<220> FEATURE:
<223> OTHER INFORMATION: The sequence is synthesized

<400> SEQUENCE: 7

Arg Ile Tyr Pro Gly Asp Gly Asp Thr Asn Tyr Asn Gly Lys Phe Lys
1               5                   10                  15

Gly

<210> SEQ ID NO 8
<211> LENGTH: 15
<212> TYPE: PRT
<213> ORGANISM: Artificial
<220> FEATURE:
<223> OTHER INFORMATION: The sequence is synthesized

<400> SEQUENCE: 8

Arg Ala Ser Lys Ser Val Ser Thr Ala Gly Tyr Ser Tyr Met His
1               5                   10                  15

<210> SEQ ID NO 9
<211> LENGTH: 155
<212> TYPE: PRT
<213> ORGANISM: Human

<400> SEQUENCE: 9

Met Asn Asn Ile Ile Asp Ile Lys Val Thr Asp Pro Gln Leu Leu Glu
1               5                   10                  15

Leu Gly Leu Val Gln Ser Pro Asp Gly His Arg Leu Tyr Val Thr Ile
                20                  25                  30

Pro Leu Gly Ile Lys Leu Gln Val Asn Thr Pro Leu Val Gly Ala Ser
            35                  40                  45

Leu Leu Arg Leu Ala Val Lys Leu Asp Ile Thr Ala Glu Ile Leu Ala
        50                  55                  60

Val Arg Asp Lys Gln Glu Arg Ile His Leu Val Leu Gly Asp Cys Thr
65                  70                  75                  80

His Ser Pro Gly Ser Leu Gln Ile Ser Leu Leu Asp Gly Leu Gly Pro
                85                  90                  95

-continued

Leu Pro Ile Gln Gly Leu Leu Asp Ser Leu Thr Gly Ile Leu Asn Lys
                100                 105                 110

Val Leu Pro Glu Leu Val Gln Gly Asn Val Cys Pro Leu Val Asn Glu
        115                 120                 125

Val Leu Arg Gly Leu Asp Ile Thr Leu Val His Asp Ile Val Asn Met
130                 135                 140

Leu Ile His Gly Leu Gln Phe Val Ile Lys Val
145                 150                 155

<210> SEQ ID NO 10
<211> LENGTH: 120
<212> TYPE: PRT
<213> ORGANISM: Artificial
<220> FEATURE:
<223> OTHER INFORMATION: The sequence is synthesized

<400> SEQUENCE: 10

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Ser Arg Ser
                20                  25                  30

Trp Met Ser Trp Val Lys Gln Arg Pro Gly Gln Gly Leu Glu Trp Ile
            35                  40                  45

Gly Arg Ile Tyr Pro Gly Asp Gly Asp Thr Lys Tyr Ser Gly Lys Phe
        50                  55                  60

Glu Gly Lys Ala Thr Leu Thr Ala Asp Lys Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Gly Gly Ile Gln Gly Tyr Gly Met Asp Tyr Trp Gly Gln
                100                 105                 110

Gly Thr Ser Val Thr Val Ser Ser
            115                 120

<210> SEQ ID NO 11
<211> LENGTH: 111
<212> TYPE: PRT
<213> ORGANISM: Artificial
<220> FEATURE:
<223> OTHER INFORMATION: The sequence is synthesized

<400> SEQUENCE: 11

Asp Ile Val Val Thr Gln Ser Pro Ala Ala Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Thr Tyr Met His Trp Tyr Gln Gln Lys Pro Gly Gln Pro Pro
            35                  40                  45

Lys Leu Leu Ile Tyr Leu Ala Ser Lys Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Asp Leu Thr Phe Gly Ser Gly Thr Lys Leu Glu Ile Lys Arg Ala
                100                 105                 110

<210> SEQ ID NO 12

<211> LENGTH: 120
<212> TYPE: PRT
<213> ORGANISM: Artificial
<220> FEATURE:
<223> OTHER INFORMATION: The sequence is synthesized

<400> SEQUENCE: 12

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Ser Arg Ser
            20                  25                  30

Trp Met Ser Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Gly Gly Ile Gln Gly Tyr Gly Met Asp Tyr Trp Gly Gln
            100                 105                 110

Gly Thr Ser Val Thr Val Ser Ser
        115                 120

<210> SEQ ID NO 13
<211> LENGTH: 111
<212> TYPE: PRT
<213> ORGANISM: Artificial
<220> FEATURE:
<223> OTHER INFORMATION: The sequence is synthesized

<400> SEQUENCE: 13

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ala
            20                  25                  30

Gly Tyr Ser Tyr Met His Trp Tyr Gln Gln Lys Pro Gly Gln Thr Pro
        35                  40                  45

Lys Leu Leu Ile Tyr Leu Ala Ser Lys Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Thr Phe Gly Ser Gly Thr Lys Leu Glu Ile Lys Arg Ala
            100                 105                 110

<210> SEQ ID NO 14
<211> LENGTH: 360
<212> TYPE: DNA
<213> ORGANISM: Artificial
<220> FEATURE:
<223> OTHER INFORMATION: The sequence is synthesized

<400> SEQUENCE: 14
caggtccagc tgcagcagtc tggacctgag ctggtgaagc ctggggcctc agtgaagatt      60
tcctgcaaaa cttctggcta cgcattcagt aggtcttgga tgagctgggt gaagcagagg     120
cctggacagg gtcttgagtg gattggacgg atttatcctg gagatggaga tacaaagtac    180

```
agtgggaagt tgagggcaa ggccacattg actgcagaca atcctccag cacagcctac    240 atgcagctca gcagcctgac ctctgtggac tctgcggtct atttctgtgc aagatcgggg    300
ggaattcaag gttatggtat ggactactgg ggtcaaggaa cctcagtcac cgtctcctca    360
```

<210> SEQ ID NO 15
<211> LENGTH: 333
<212> TYPE: DNA
<213> ORGANISM: Artificial
<220> FEATURE:
<223> OTHER INFORMATION: The sequence is synthesized

<400> SEQUENCE: 15

```
gacattgtgg tgacacagtc tcctgctgcc ttagctgtat ctctgggca gagggccacc    60 atctcatgca gggccagcaa aagtgtcagt acatctggct atacttatat gcactggtac    120
caacagaaac caggacagcc acccaaactc ctcatctatc ttgcatccaa gctagaatct    180
ggggtcccag ccaggttcag tggcagtggg tctgggacag acttcaccct caacatccat    240
cctgtggagg aggaggatgc tgcaacctat tactgtcagc acagtaggga cctcacgttc    300
ggctcgggga caaagttgga aataaaacgg gct                                333
```

<210> SEQ ID NO 16
<211> LENGTH: 360
<212> TYPE: DNA
<213> ORGANISM: Artificial
<220> FEATURE:
<223> OTHER INFORMATION: The sequence is synthesized

<400> SEQUENCE: 16

```
caggtccagt tgcagcagtc tggacctgag ctggtgaagc ctggggcctc agtgaagatt    60
tcctgcaaaa cttctggcta cgcattcagt aggtcttgga tgagttgggt gaagcagagg    120
cctggacagg gtcttgagtg gattggacgg atttatcctg agatggaga tactaactac    180 aatgggaagt tcaagggcaa ggccacactg actgcagaca atcctccag cacagcctac    240 atgcaactca gcagcctgac ctctgtggac tctgcggtct atttctgtgc aagatcgggg    300
ggaattcaag ggtatggtat ggactactgg ggtcaaggaa cctcagtcac cgtctcctca    360
```

<210> SEQ ID NO 17
<211> LENGTH: 333
<212> TYPE: DNA
<213> ORGANISM: Artificial
<220> FEATURE:
<223> OTHER INFORMATION: The sequence is synthesized

<400> SEQUENCE: 17

```
gacattgtgc tgacacagtc tcctgcttcc ttagctgtat ctctgggca gagggccacc    60 atctcatgca gggccagcaa aagtgtcagt acagctggct atagttatat gcactggtac    120
caacagaaac caggacagac acccaaactc ctcatctatc ttgcatccaa gctagaatct    180
ggggtccctg ccaggttcag tggcagtggg tctgggacag acttcaccct caacatccat    240
cctgtggagg aggaggatgc tgcaacctat tactgtcagc acagtaggga gctcacgttc    300
ggctcgggga caaagttgga aataaaacgg gct                                333
```

<210> SEQ ID NO 18
<211> LENGTH: 478
<212> TYPE: PRT
<213> ORGANISM: Artificial
<220> FEATURE:
<223> OTHER INFORMATION: The sequence is synthesized

<400> SEQUENCE: 18

```
Asp Ile Val Val Thr Gln Ser Pro Ala Ala Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Lys Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Asp Leu Thr Phe Gly Ser Gly Thr Lys Leu Glu Ile Lys Arg Ala Gly
            100                 105                 110

Gly Gly Gly Ser Gly Gly Gly Gly Ser Gly Gly Gly Gly Ser Gln Val
        115                 120                 125

Gln Leu Gln Gln Ser Gly Pro Glu Leu Val Lys Pro Gly Ala Ser Val
    130                 135                 140

Lys Ile Ser Cys Lys Thr Ser Gly Tyr Ala Phe Ser Arg Ser Trp Met
145                 150                 155                 160

Ser Trp Val Lys Gln Arg Pro Gly Gln Gly Leu Glu Trp Ile Gly Arg
                165                 170                 175

Ile Tyr Pro Gly Asp Gly Asp Thr Lys Tyr Ser Gly Lys Phe Glu Gly
            180                 185                 190

Lys Ala Thr Leu Thr Ala Asp Lys Ser Ser Thr Ala Tyr Met Gln
    195                 200                 205

Leu Ser Ser Leu Thr Ser Val Asp Ser Ala Val Tyr Phe Cys Ala Arg
210                 215                 220

Ser Gly Gly Ile Gln Gly Tyr Gly Met Asp Tyr Trp Gly Gln Gly Thr
225                 230                 235                 240

Ser Val Thr Val Ser Ser Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

Lys Val Ser Asn Lys Ala Leu Pro Ala Pro Ile Glu Lys Thr Ile Ser
        355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
```

```
                    405                 410                 415
Gln Pro Glu Asn Asn Tyr Lys Thr Thr Pro Val Leu Asp Ser Asp
                420                 425                 430

Gly Ser Phe Phe Leu Tyr Ser Lys Leu Thr Val Asp Lys Ser Arg Trp
            435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475
```

<210> SEQ ID NO 19
<211> LENGTH: 478
<212> TYPE: PRT
<213> ORGANISM: Artificial
<220> FEATURE:
<223> OTHER INFORMATION: The sequence is synthesized

<400> SEQUENCE: 19

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ala
            20                  25                  30

Gly Tyr Ser Tyr Met His Trp Tyr Gln Gln Lys Pro Gly Gln Thr Pro
        35                  40                  45

Lys Leu Leu Ile Tyr Leu Ala Ser Lys Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Thr Phe Gly Ser Gly Thr Lys Leu Glu Ile Lys Arg Ala Gly
            100                 105                 110

Gly Gly Gly Ser Gly Gly Gly Gly Ser Gly Gly Gly Gly Ser Gln Val
        115                 120                 125

Gln Leu Gln Gln Ser Gly Pro Glu Leu Val Lys Pro Gly Ala Ser Val
    130                 135                 140

Lys Ile Ser Cys Lys Thr Ser Gly Tyr Ala Phe Ser Arg Ser Trp Met
145                 150                 155                 160

Ser Trp Val Lys Gln Arg Pro Gly Gln Gly Leu Glu Trp Ile Gly Arg
                165                 170                 175

Ile Tyr Pro Gly Asp Gly Asp Thr Asn Tyr Asn Gly Lys Phe Lys Gly
            180                 185                 190

Lys Ala Thr Leu Thr Ala Asp Lys Ser Ser Thr Ala Tyr Met Gln
        195                 200                 205

Leu Ser Ser Leu Thr Ser Val Asp Ser Ala Val Tyr Phe Cys Ala Arg
    210                 215                 220

Ser Gly Gly Ile Gln Gly Tyr Gly Met Asp Tyr Trp Gly Gln Gly Thr
225                 230                 235                 240

Ser Val Thr Val Ser Ser Glu Pro Lys Ser Cys Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
```

```
            290                 295                 300
Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
                340                 345                 350

Lys Val Ser Asn Lys Ala Leu Pro Ala Pro Ile Glu Lys Thr Ile Ser
                355                 360                 365

Lys Ala Lys Gly Gln Pro Arg Glu Pro Gln Val Tyr Thr Leu Pro Pro
    370                 375                 380

Ser Arg Asp Glu Leu Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
                420                 425                 430

Gly Ser Phe Phe Leu Tyr Ser Lys Leu Thr Val Asp Lys Ser Arg Trp
                435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475

<210> SEQ ID NO 20
<211> LENGTH: 232
<212> TYPE: PRT
<213> ORGANISM: human

<400> SEQUENCE: 20

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 21
<211> LENGTH: 696
<212> TYPE: DNA
<213> ORGANISM: human

<400> SEQUENCE: 21
gagcccaaat cttgtgacaa aactcacaca tgcccaccgt gcccagcacc tgaactcctg      60
gggggaccgt cagtcttcct cttccccca  aaacccaagg acaccctcat gatctcccgg     120 accctgagg  tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa  gaccacgcct     540 cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggtaaa                               696

<210> SEQ ID NO 22
<211> LENGTH: 45
<212> TYPE: DNA
<213> ORGANISM: Artificial
<220> FEATURE:
<223> OTHER INFORMATION: The sequence is synthesized

<400> SEQUENCE: 22
ggcggcggcg gcagcggcgg cggcggcagc ggcggcggcg gcagc                      45
```

ANTIBODY OR ANTIBODY FRAGMENT CAPABLE OF BINDING TO LUNG-SPECIFIC X PROTEIN AND USE THEREOF

CROSS REFERENCE TO RELATED APPLICATIONS

This application is a 35 USC § 371 national stage application of PCT/CN2017/085836, which was filed May 25, 2017 and claimed priority to CN 201710004133.X, which was filed Jan. 4, 2017, both of which are incorporated herein by reference as if fully set forth.

FIELD OF THE INVENTION

The present invention relates to the field of antibodies, and in particular, relates to an antibody or antibody fragment capable of binding to lung-specific X protein and uses thereof.

BACKGROUND OF THE INVENTION

Since the 21st century, antibody therapy has made rapid progress and has become one of the most successful and important strategies for the treatment of malignant tumors. Monoclonal antibody drugs have become a hotspot of molecular targeted therapy research because of their high specificity and low toxicity. Clinical practice has shown that tumor therapy has entered into an unprecedented new stage due to the outstanding efficacy of monoclonal antibodies.

Lung cancer is one of the malignant tumors with the highest incidence and mortality in recent years. The 5-year survival rate thereof is only 13%. Therefore, it is urgent to find an effective biotherapeutic targets for lung cancer to facilitate the treatment of targeting monoclonal antibody drugs for lung cancer. At present, lung cancer is mainly divided into small cell lung cancer and non-small cell lung cancer clinically, and more than 85% of them are non-small cell lung cancer. A large number of studies have confirmed that mRNA of the lung-specific X protein (LunX) can be used as a specific biomarker for the diagnosis of lung cancer, it's mainly expressed on the surface of non-small cell lung cancer, and the positive rate reaches 90%. It is also found that patients with higher LunX protein expression show worse pathological stage, lower differentiation status and less survival time. In addition, LunX expression is not detected in normal peripheral lung tissues and other organs such as breast, liver, and ovary. (Xiaohu ZHENG et al., Cancer Res, 75(6); 1080-90.2015 AACR; Lynne Bingle et al., J Pathol; 2005; 205: 491-497).

The lung-specific X protein (LunX), belonging to the PLUNC family, is a human lung tissue-specific X protein discovered in 2001 by the Iwao research team using differential display technology for RNA isolated from 13 different tissues of human bodies. The gene is located at 20p11.1q12, and is 1015 bp in length and includes an open reading frame with 768 nucleotides which encodes 256 amino acids.

The function of overexpression of LunX in lung cancer mainly confirms that LunX promotes the proliferation, migration and invasion of tumor cells, and targeted interference of LunX can significantly inhibit the occurrence and development of tumors. The LunX acts on the tumor-associated protein 14-3-3, it promotes the formation of homodimer or heterodimer in an activated state, then activates the downstream Erk1/2 and JNK signaling pathways, and ultimately leads to the proliferation and metastasis of tumor cells (Xiaohu ZHENG et al., Cancer Res; 75(6)).

Therefore, antibodies targeting to LunX may be potential drugs for the treatment of lung cancer. Studies have reported that murine monoclonal antibodies can be used in humans to produce strong immunogenicity, which can cause rejection of heterologous proteins and produce human anti-mouse antibody (HAMA) responses. Multiple uses may lead to anaphylactic shock in patients, and other side effects are reflected in rapid elimination of murine antibodies in vivo, cardiac toxicity, rapid drug resistance and the like. In view of this, the antibody structure can be engineered using antibody engineering techniques. Animal-derived monoclonal humanization is intended to reduce their immunogenicity and simultaneously ensure antibody specificity.

Currently, monoclonal antibodies against tumor-targeting antigens can exert anti-tumor effects through two mechanisms. One is a direct mechanism, in which the antibody binds to the antigen on the surface of the tumor cell to change the activated form of the antigen or the degradation of the antigen, thereby blocking the activation of the corresponding downstream cancer-promoting signaling pathway, and finally inhibiting the proliferation and metastasis of the tumor cell. The other is an indirect mechanism which is primarily achieved through activation of immune responses, including antibody-dependent cell-mediated cytotoxicity (ADCC) and complement dependent cytotoxicity (CDC). In order to obtain better anti-tumor effects, anti-tumor drugs are expected to exert anti-tumor effects through various mechanisms as described above. Therefore, it is particularly necessary to develop anti-LunX antibodies capable of mediating various anti-tumor mechanisms.

SUMMARY OF THE INVENTION

It is an object of the present invention to overcome the deficiencies of the prior art, and to provide an antibody or antibody fragment capable of mediating a variety of anti-tumor mechanisms and uses thereof.

In order to achieve the object, in the first aspect, the present invention provides an antibody or antibody fragment capable of binding to lung-specific X protein, the antibody or antibody fragment comprises heavy chain CDRs with amino acid sequences of SEQ ID NO: 1, SEQ ID NO: 2 and SEQ ID NO: 3 and light chain CDRs with amino acid sequences of SEQ ID NO: 4, SEQ ID NO: 5 and SEQ ID NO: 6;

or comprises heavy chain CDRs with amino acid sequences of SEQ ID NO: 1, SEQ ID NO: 7 and SEQ ID NO: 3 and light chain CDRs with amino acid sequences of SEQ ID NO: 8, SEQ ID NO: 5 and SEQ ID NO: 6.

In the second aspect, the present invention provides a composition comprising the antibodies or antibody fragments described in the first aspect and pharmaceutically acceptable carriers.

In the third aspect, the present invention provides a kit for detecting a lung-specific X protein in a sample. The kit includes the antibodies or antibody fragments described in the first aspect.

In the fourth aspect, the present invention provides use of the antibody or antibody fragment described in the first aspect for the preparation of a reagent for detecting a lung-specific X protein in a sample.

In the fifth aspect, the present invention provides use of the antibody or antibody fragment described in the first aspect for the preparation of a medicament for inhibiting cancer cells.

In the sixth aspect, the present invention provides a nucleic acid encoding the antibody or antibody fragment described in the first aspect.

In the seventh aspect, the present invention provides a recombinant vector or transformant containing the nucleic acid described in the sixth aspect.

According to above technical solutions, the antibody or antibody fragment of the present invention is capable of mediating a plurality of anti-tumor mechanisms, and the anti-tumor effect of which is favorable. Moreover, the inventors of the present invention further humanize the antibody or antibody fragment, and the specificity and antitumor activity of the resulting chimeric antibody, or humanized antibody or antibody fragment still maintain at a preferred level.

Other features and advantages of the present invention will be further detailed in the embodiments hereunder.

BRIEF DESCRIPTION OF THE DRAWINGS

The accompanying drawings are provided here to facilitate further understanding on the present invention, and constitute a part of the description. They are used in conjunction with the following embodiments to explain the present invention, but shall not be comprehended as constituting any limitation to the present invention. In the figures.

DETAILED DESCRIPTION OF THE EMBODIMENTS

Figure 1:
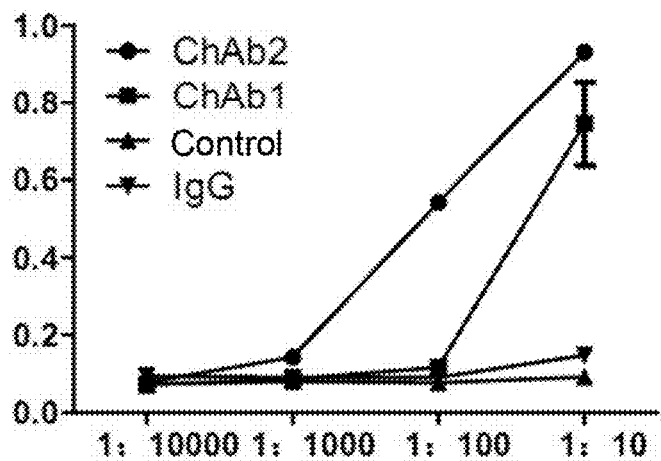
FIG. 1 shows the results of ELISA analysis of a chimeric antibody in one embodiment of the present invention.

Some embodiments of the present invention will be described in detail below. It should be understood that the embodiments described here are only provided to describe and explain the present invention, but shall not be deemed as constituting any limitation to the present invention.

The end-points and any value in the ranges disclosed in the present invention are not limited to the exact ranges or values; instead, those ranges or values shall be comprehended as encompassing values that are close to those ranges or values. For numeric ranges, the endpoint values of the various ranges, the endpoint values of the ranges and the discrete point values, as well as the discrete point values may be combined to obtain one or more new numeric ranges, which shall be deemed as having been disclosed specifically in this document.

In the present invention, the term "antibody fragment" as used herein generally refers to an antigen-binding antibody fragment, and may include a part of an intact antibody, is generally an antigen-binding region or a variable region, unless otherwise specified. Examples of the antibody fragment include Fab, Fab', F(ab')$_2$, Fv or scFv, diabody, linear antibody, single-chain antibody molecule and the like.

The term "complementarity determining region" or "amino acid sequence of CDR" or "CDR sequence" refers to an amino acid sequence in an antibody responsible for binding to an antigen, for example, it typically comprising: amino acid residues near 23-34 (L1), 50-56 (L2), and 89-97 (L3) in the light chain variable region, and amino acid residues near 31-35B (H1), 50-65 (H2) and 95-102 (H3) in the heavy chain variable region (Kabat et al., Sequences of Proteins of Immunological Interest, 5$^{th}$ Ed. Public Health Service, National Institutes of Health, Bethesda, Md. (1991)); and/or amino acid residues from "hypervariable loops" (e.g., amino acid residues near 26-32 (L1), 50-52 (L2), and 91-96 (L3) in the light chain variable region, and 26-32 (H1), 53-55 (H2), and 96-101 (H3) in the heavy chain variable region (Chothia and Lesk J. Mol. Biol. 196: 901-917 (1987)).

The antibody or antibody fragment capable of binding to a lung-specific X protein provided by the present invention comprises heavy chain CDRs with amino acid sequences of SEQ ID NO: 1, SEQ ID NO: 2 and SEQ ID NO: 3 (N-terminal to C-terminal) and light chain CDRs with amino acid sequences of SEQ ID NO: 4, SEQ ID NO: 5 and SEQ ID NO: 6 (N-terminal to C-terminal);

or comprises heavy chain CDRs with amino acid sequences of SEQ ID NO: 1, SEQ ID NO:7 and SEQ ID NO: 3 (N-terminal to C-terminal) and light chain CDRs with amino acid sequences of SEQ ID NO: 8, SEQ ID NO: 5 and SEQ ID NO: 6 (N-terminal to C-terminal).

In the present invention, the antibody or antibody fragment is capable of binding to a lung-specific X protein (antigen), particularly, is capable of binding to the amino acid sequence shown in SEQ ID NO: 9 below. Preferably, the affinity constant (K) of the antibody or antibody fragment of the present invention with the lung-specific X protein is $8 \times 10^8$ or more. The term "affinity constant" indicates the closeness degree of antibody binding to the antigen, which can be measured by competitive ELISE method. The formula is: $K=1/Kd$ and $A_0/(A_0-A)=1+Kd/a_0$, in which $A_0$ is the OD value when the concentration of competitive antigen is 0, A is the OD value under each antigen concentration, $a_0$ is the total amount of antigen, and Kd is dissociation constant.

```
                                                       (SEQ ID NO: 9)
MNNIIDIKVT DPQLLELGLV QSPDGHRLYV TIPLGIKLQV NTPLVGASLL RLAVKLDITA   60

EILAVRDKQE RIHLVLGDCT HSPGSLQISL LDGLGPLPIQ GLLDSLTGIL NKVLPELVQG  120

NVCPLVNEVL RGLDITLVHD IVNMLIHGLQ FVIKV                             155
```

In a preferred embodiment of the present invention, the amino acid sequence of the heavy chain variable region of the antibody or antibody fragment is shown in SEQ ID NO: 10 or SEQ ID NO: 12.

In another preferred embodiment of the invention, the amino acid sequence of the light chain variable region of the antibody or antibody fragment is shown in SEQ ID NO: 11 or SEQ ID NO: 13. As shown previously (SEQ ID NO: 6), the amino acid sequence of the light chain variable region of the antibody or antibody fragment may also be shown by the amino acid sequence obtained by replacing the aspartic acid residue (D) at position 97 of SEQ ID NO: 11 with glutamic acid residue (E), or be shown by the amino acid sequence obtained by replacing the glutamic acid residue (E) at position 97 of SEQ ID NO: 13 with aspartic acid residue (D).

According to a most preferred embodiment of the present invention, the amino acid sequence of the heavy chain variable region of the antibody or antibody fragment is shown in SEQ ID NO: 10 and the amino acid sequence of the light chain variable region thereof is shown in SEQ ID NO: 11. Alternatively, the amino acid sequence of the heavy chain variable region of the antibody or antibody fragment is shown in SEQ ID NO: 12 and the amino acid sequence of the light chain variable region thereof is shown in SEQ ID NO: 13.

In a preferred embodiment of the invention, in order to further increase the bio-acceptability of the antibody, the antibody may further be humanized, i.e., the antibody is a chimeric antibody or a humanized antibody. The term "chimeric antibody" refers to a recombinant antibody obtained by replacing the amino acid sequence in constant region of a monoclonal antibody from one species (e.g., mice) with the constant region of an antibody from another species (e.g., human) (e.g., SEQ ID NO: 20, which is encoded by nucleic acid shown in SEQ ID NO:21), using recombinant DNA technology. The term "humanized antibody" refers to a recombinant antibody obtained by replacing the constant region and non-CDR amino acid sequences (Fv framework region (FR)) of the variable regions of a monoclonal antibody from a species (e.g., mice) with the constant region and non-CDR amino acid sequences of the variable regions of an antibody from another species (e.g., human), using recombinant DNA technology. That is, it is referred to as a chimeric antibody when the constant region of an antibody is humanized, and referred to as a humanized antibody when the constant region and non-CDR amino acid sequences of the variable region are all humanized. The method of humanization can be carried out in accordance with conventional antibody engineering techniques and will not be described herein.

For example, the amino acid sequence of the chimeric antibody provided by the present invention may be shown in SEQ ID NO: 18 or SEQ ID NO: 19 as follows:

```
                                                                (SEQ ID NO: 18)
        DIVVTQSPAA LAVSLGQRAT ISCRASKSVS TSGYTYMHWY QQKPGQPPKL LIYLASKLES  60

GVPARFSGSG SGTDFTLNIH PVEEEDAATY YCQHSRDLTF GSGTKLEIKR AGGGGSGGGG 120

SGGGGSQVQL QQSGPELVKP GASVKISCKT SGYAFSRSWM SWVKQRPGQG LEWIGRIYPG 180

DGDTKYSGKF EGKATLTADK SSSTAYMQLS SLTSVDSAVY FCARSGGIQG YGMDYWGQGT 240

SVTVSSEPKS CDKTHTCPPC PAPELLGGPS VFLFPPKPKD TLMISRTPEV TCVVVDVSHE 300

DPEVKFNWYV DGVEVHNAKT KPREEQYNST YRVVSVLTVL HQDWLNGKEY KCKVSNKALP 360

APIEKTISKA KGQPREPQVY TLPPSRDELT KNQVSLTCLV KGFYPSDIAV EWESNGQPEN 420

NYKTTPPVLD SDGSFFLYSK LTVDKSRWQQ GNVFSCSVMH EALHNHYTQK SLSLSPGK   478

(SEQ ID NO: 19)
        DIVLTQSPAS LAVSLGQRAT ISCRASKSVS TAGYSYMHWY QQKPGQTPKL LIYLASKLES  60

GVPARFSGSG SGTDFTLNIH PVEEEDAATY YCQHSRELTF GSGTKLEIKR AGGGGSGGGG 120

SGGGGSQVQL QQSGPELVKP GASVKISCKT SGYAFSRSWM SWVKQRPGQG LEWIGRIYPG 180

DGDTNYNGKF KGKATLTADK SSSTAYMQLS SLTSVDSAVY FCARSGGIQG YGMDYWGQGT 240

SVTVSSEPKS CDKTHTCPPC PAPELLGGPS VFLFPPKPKD TLMISRTPEV TCVVVDVSHE 300

DPEVKFNWYV DGVEVHNAKT KPREEQYNST YRVVSVLTVL HQDWLNGKEY KCKVSNKALP 360

APIEKTISKA KGQPREPQVY TLPPSRDELT KNQVSLTCLV KGFYPSDIAV EWESNGQPEN 420

NYKTTPPVLD SDGSFFLYSK LTVDKSRWQQ GNVFSCSVMH EALHNHYTQK SLSLSPGK   478
```

The composition provided by the present invention contains above antibodies or antibody fragments and pharmaceutically acceptable carriers.

The term "pharmaceutically acceptable" indicates that the composition is capable of being administered to a subject without producing an undesirable physiological response that would interfere with administration of the composition. For example, "pharmaceutically acceptable carrier" refers to a carrier that is useful in the preparation of a pharmaceutical composition that is generally safe, non-toxic, and desirable. Preferably, examples of such carriers or diluents include, but not limited to, water, saline, Ringer's solution, glucose solution and 5% human serum albumin; and liposomes and non-aqueous vehicles such as fixed oils may also be used.

The composition of the present invention may also be administered in combination with one another, or be administered in combination with one or more other therapeutic compounds; for example, it can be administered in combination with a chemotherapeutic agent. Thus, said composition may also contain a chemotherapeutic agent.

Typically, the antibody or antibody fragment is administered in a therapeutically effective amount, i.e., an amount sufficient to achieve desired therapeutic and/or prophylactic effect, for example, an amount that realizes the prevention or the alleviation of symptoms associated with the disease being treated. The disease is, for example, a disease associated with a lung-specific X protein. The therapeutically effective amount of the composition administered to a subject depends on the type and severity of the disease, as well as depends on the characteristics of the individual, such as general health state, age, sex, weight, and tolerance to the drug; and also depends on the severity and type of the disease. Those skilled in the art will be able to determine the appropriate dosage based on these factors and the like.

The kit for detecting a lung-specific X protein in a sample provided by the present invention includes above antibodies or antibody fragments. The sample may be tissues of a cancer patient (particularly lung cancer patient, more preferably non-small cell lung cancer patient), such as lung tissue or subclavian lymph node tissue. The kit may further include a reagent conventionally used for detecting a lung-specific X protein, such as a coating buffer or the like.

The invention also provides use of above antibody or antibody fragment for the preparation of a reagent for detecting a lung-specific X protein in a sample. As mentioned previously, the sample may be tissues of a cancer patient (particularly lung cancer patient, more preferably non-small cell lung cancer patient), such as lung tissue or subclavian lymph node tissue. The antibody or antibody fragment of the present invention has a good affinity with the lung-specific X protein, and is capable of efficiently detecting a lung-specific X protein in a sample.

The present invention also provides use of above antibody or antibody fragment for the preparation of a medicament for inhibiting cancer cells. The cancer cells are preferably lung cancer cells, more preferably non-small cell lung cancer cells.

Moreover, the present invention further relates to a method for inhibiting cancer cells in vitro, which comprises contacting the cancer cells (as described above) with an effective amount of the antibody or antibody fragment or the composition of the present invention.

The invention further relates to a method for inhibiting cancer cells (as described above) in a patient, which comprises administering a therapeutically effective amount of the antibody or antibody fragment or composition of the present invention to the patient. Wherein, the way of administration may be intravenous administration and/or intraperitoneal administration.

The term "inhibiting" as used includes inhibiting the proliferation, growth and/or metastasis of cancer cells. A "patient" or "subject" as used in the present invention generally refers to mammals, such as primates and/or rodents, particularly human or mice.

The invention also provides (isolated) nucleic acids encoding above antibody or antibody fragments, as well as recombinant vectors and transformants containing said nucleic acids. The nucleic acid is preferably an expression cassette obtained by genetic engineering means.

Nucleic acids encoding the heavy chain and/or light chain of the antibody or antibody fragments of the invention are within the scope of the present invention, and those skilled in the art will readily be able to obtain the corresponding nucleic acid sequences based on the amino acid sequences of the heavy chain and/or light chain; for example, the base sequence of the nucleic acid encoding the heavy chain of the antibody or antibody fragment is shown in SEQ ID NO: 14 or SEQ ID NO: 16, and the base sequence of the nucleic acid encoding the light chain of the antibody or antibody fragment is shown in SEQ ID NO: 15 or SEQ ID NO: 17.

The recombinant vector may refer to a cloning vector, and may also refer to an expression vector, which can be obtained by operably linking said nucleic acids to a commercially available vector (such as a plasmid or a viral vector). Commonly used plasmids include PSeTag2, PEE 14, pMH3 and the like.

The transformant can be obtained by transforming above nucleic acids or the recombinant vector into a host cell. The host cell may be various cells conventionally used, such as CHO-K1, CHO—S and the like.

The present invention will be described in detail in the following example. In the examples or the test examples, the experimental methods which do not specify the specific conditions are carried out in accordance with conventional conditions.

Example 1

(I) Preparation of Anti-LunX Monoclonal Antibody

Anti-LunX monoclonal antibody is prepared with reference to slightly modified conventional hybridoma cell fusion technique (St Groth and Sheidegger 1980, J Immunol Methods 35:1-21; Kohler and Milstein, 1976, European J of Immunol 6:511-519; Mechetner 2007, Methods mol Biol 378:1-13), as follows. Monoclonal antibody with high binding activity in enzyme-linked immunosorbent assay (ELISA) and flow cytometry (FACS) are selected for further analysis.

(1) Recombinant LunX Protein for Immunization and Binding Identification

The full-length LunX gene is synthesized (NCBI Reference Sequence: NM 016583.3). The antigenic protein fragment shown in SEQ ID NO: 9 are amplified by PCR. 6His-Tag and stop codon are introduced at C-terminus of the target sequence and cloned into pET-22b(+) vector (Novagen), and transferred to competent bacteria Rosetta (DE3) (Novagen, Cat. No. 70954-3). Then the LunX prokaryotic recombinant fusion protein expressing plasmid pET22b-LunX is produced. The selected monoclonal colonies are inoculated into LB medium, placed in a shaker at 37° C., and cultured at 200 rpm until OD600 nm=0.6-0.8, added with 1 mM isopropyl-β-D-thiogalactoside (IPTG), and continue to be cultured for 4-6 hours to induce protein expression. The cells are collected by centrifugation at 6,000 g for 10 minutes at 4° C., and the precipitate is washed with a lysis buffer (50 mM Tris, 100 mM NaCl, pH 8.5), and then lysed by a high-pressure crushing method. The lysate mixture is purified by nickel column affinity chromatography, and the target protein is eluted with different concentrations of imidazole. The target recombinant protein of certain purity is obtained in 100 mM imidazole eluate (50 mM Tris, 100 mM NaCl, 200 mM imidazole, pH 9). It is further purified by molecular sieve chromatography (S-200), and the recombinant protein having a purity of more than 90% and a concentration of 1 mg/ml is eluted. Mass spectrometry identification shows that the peptide of the target protein matched the LunX sequence, which proves that the recombinant protein is a recombinant LunX protein.

(2) Animal Immunization, Hybridoma Cell Fusion and Clone Screening

The LunX protein is well mixed with an equal volume of complete Freund's adjuvant (CFA). The 8-10 weeks-old BALB/c female mice (purchased from Shanghai SLAC, weighing about 20 g) are immunized for the first time, and each mouse is intraperitoneally injected with 40-60 μg LunX protein, and immunized once every 2 weeks. The same dose of LunX protein is mixed with an equal volume of incomplete Freund's adjuvant. After immunizing for 5 times, the serum titer of the mice is not lower than 1:105 by ELISA, 40-60 μg of LunX protein is finally injected for enhancement. On the third day after enhancement, the splenocytes are isolated using standard technique (Gefter, M. L. et al, 1977 Somat Cell Genet, 3:231-236) and fused with mouse myeloma cells SP2/0 cells (ATCC No. CRL-1581). Hybridoma cells which show positive signals by both ELISA and FACS are subjected to subclone screening to obtain two hybridoma cells Ab2 and Ab1.

(3) Expression and Purification of Monoclonal Antibody

Monoclonal antibody is prepared by intraperitoneal inoculation of mice. 8-10 weeks-old BALB/C mice are immunized by intraperitoneal injection 500 μl of sterile liquid paraffin firstly, and are intraperitoneally injected with $1 \times 10^6$ hybridoma cells after one week. The ascites of the mice are collected after about 7-10 days. The supernatant is collected by high speed centrifugation of the ascites. The antibody obtained by above method is purified by Protein A affinity chromatography (GE Life Sciences), and the purity of the two purified monoclonal antibodies (PrAb2 and PrAb1) is higher than 95%. The molecular weight of heavy chain of the antibody is about 45 kDa, the light chain thereof is about 25 kDa.

(II) Variable Region Sequence of Anti-LunX Monoclonal Antibody

When the total number of candidate hybridoma cells is cultured to $10^6$, the cells are collected by centrifugation at 800 rpm for 10 minutes. Total RNA is extracted from the cells using a Trizol kit (Invitrogen). The cDNA library (Invitrogen) is synthesized by reverse transcription using the total RNA as a template. The corresponding variable region nucleic acid sequence of the hybridoma cells is PCR amplified using cDNA as a template. The primer sequence used in the PCR amplification reaction is complementary to the first framework region or the signal peptide region of the variable region and the constant region of the antibody (Larrick, J. W., et al., (1990) Scand. J. Immunol., 32, 121-128 and Coloma, J. J. et al., (1991) BioTechniques, 11, 152-156). 50 μl reaction system is added with 2 μl of cDNA, 5 μl of 10×PCR buffer, 2 μl (5 μmol) of upstream and downstream primers, 2 μl of dNTP, 1 μl of Taq enzyme (Takara, Ex Taq), 38 μl of H₂O; and then pre-denatured at 95° C. for 5 min, and entered temperature cycle to perform PCR amplification. The reaction conditions are: denaturation at 94° C. for 30 s, annealing at 58° C. for 45 s, extension at 72° C. for 50 s, 32 cycles, and then extension at 72° C. for 7 min. After sequencing the amplified products, the heavy and light chain variable region sequences (including amino acid sequence and nucleic acid sequence) of the hybridoma cells Ab2 and Ab1 are obtained as shown in Table 1 below, and the bolded and underlined fragments of the sequences shown in Table 1 are CDR amino acid sequences:

TABLE 1

| | Ab2 | Ab1 |
|---|---|---|
| Heavy chain | Amino acid sequence:<br>QVQLQQSGPELVKPGASVKI<br>SCKTSGYAFSRSWMSWVKQR<br>PGQGLEWIGRIYPGDGDTKY<br>SGKFEGKATLTADKSSSTAY<br>MQLSSLTSVDSAVYFCARSG<br>GIQGYGMDYWGQGTSVTVSS<br>(SEQ ID NO: 10) | Amino acid sequence:<br>QVQLQQSGPELVKPGASVKI<br>SCKTSGYAFSRSWMSWVKQR<br>PGQGLEWIGRIYPGDGDTNY<br>NGKFKGKATLTADKSSSTAY<br>MQLSSLTSVDSAVYFCARSG<br>GIQGYGMDYWGQGTSVTVSS<br>(SEQ ID NO: 12) |
| | Nucleic acid sequence:<br>CAGGTCCAGCTGCAGCAGTC<br>TGGACCTGAGCTGGTGAAGC<br>CTGGGGCCTCAGTGAAGATT<br>TCCTGCAAAACTTCTGGCTA<br>CGCATTCAGTAGGTCTTGGA<br>TGAGCTGGGTGAAGCAGAGG<br>CCTGGACAGGGTCTTGAGTG<br>GATTGGACGGATTTATCCTG<br>GAGATGGAGATACAAAGTAC<br>AGTGGGAAGTTTGAGGGCAA<br>GGCCACATTGACTGCAGACA<br>AATCCTCCAGCACAGCCTAC<br>ATGCAGCTCAGCAGCCTGAC<br>CTCTGTGGACTCTGCGGTCT<br>ATTTCTGTGCAAGATCGGGG<br>GGAATTCAAGGTTATGGTAT<br>GGACTACTGGGGTCAAGGAA<br>CCTCAGTCACCGTCTCCTCA<br>(SEQ ID NO: 14) | Nucleic acid sequence:<br>CAGGTCCAGTTGCAGCAGTC<br>TGGACCTGAGCTGGTGAAGC<br>CTGGGGCCTCAGTGAAGATT<br>TCCTGCAAAACTTCTGGCTA<br>CGCATTCAGTAGGTCTTGGA<br>TGAGTTGGGTGAAGCAGAGG<br>CCTGGACAGGGTCTTGAGTG<br>GATTGGACGGATTTATCCTG<br>GAGATGGAGATACTAACTAC<br>AATGGGAAGTTCAAGGGCAA<br>GGCCACACTGACTGCAGACA<br>AATCCTCCAGCACAGCCTAC<br>ATGCAACTCAGCAGCCTGAC<br>CTCTGTGGACTCTGCGGTCT<br>ATTTCTGTGCAAGATCGGGG<br>GGAATTCAAGGGTATGGTAT<br>GGACTACTGGGGTCAAGGAA<br>CCTCAGTCACCGTCTCCTCA<br>(SEQ ID NO: 16) |
| Light chain | Amino acid sequence:<br>DIVVTQSPAALAVSLGQRAT<br>ISCRASKSVSTSGYTYMHWY<br>QQKPGQPPKLLIYLASKLES<br>GVPARFSGSGSGTDFTLNIH<br>PVEEEDAATYYCQHSRDLTF<br>GSGTKLEIKRA<br>(SEQ ID NO: 11) | Amino acid sequence:<br>DIVLTQSPASLAVSLGQRAT<br>ISCRASKSVSTAGYSYMHWY<br>QQKPGQTPKLLIYLASKLES<br>GVPARFSGSGSGTDFTLNIH<br>PVEEEDAATYYCQHSRELTF<br>GSGTKLEIKRA<br>(SEQ ID NO: 13) |
| | Nucleic acid sequence:<br>GACATTGTGGTGACACAGTC<br>TCCTGCTGCCTTAGCTGTAT<br>GGGGCAGAGGGCCACCATCT<br>CACTCTTGCAGGGCCAGCAA<br>AAGTGTCAGTACATCTGGCT<br>GCACTGGTACCAACAGAAAC<br>GGACAGCCACCCAAACTCCT<br>TCTATCTTGCATCCAAGCTA<br>GACACAATACTTATATATCT<br>GGGGTCCCAGCCAGGTTCAG<br>TGGCAGTGGGTCTGGGACAG<br>ACTTCACCCTCAACATCCAT<br>CCTGTGGAGGAGGAGGATGC<br>ACCTATTACTGTCAGCACAG<br>GGGACCTCACGTTCGGCTCG<br>GACAAAGTTGGAAATAAAAC<br>GGGGTATGCAGCT<br>(SEQ ID NO: 15) | Nucleic acid sequence:<br>GACATTGTGCTGACACAGTC<br>TCCTGCTTCCTTAGCTGTAT<br>GGGGCAGAGGGCCACCATCT<br>TGCAGGGCCAGCAAAAGTGT<br>GTACAGCTGGCTATAGTTAT<br>GCACTGGTACCAACAGAAAC<br>GGACAGACACCCAAACTCCT<br>TCTATCTTGCATCCAAGCTA<br>GACACAATCACACTCTATCT<br>GGGGTCCCTGCCAGGTTCAG<br>TGGCAGTGGGTCTGGGACAG<br>ACTTCACCCTCAACATCCAT<br>CCTGTGGAGGAGGAGGATGC<br>ACCTATTACTGTCAGCACAG<br>GGGAGCTCACGTTCGGCTCG<br>GACAAAGTTGGAAATAAAAC<br>GGGGTATGCAGCT<br>(SEQ ID NO: 17) |

TABLE 1-continued

| | Ab2 | Ab1 |
|---|---|---|
| Nucleic acid sequence of chimeric antibody | Nucleic acid sequence of light chain(SEQ ID NO: 15)-linking sequence (SEQ ID NO: 22)-nucleic acid sequence of heavy chain(SEQ ID NO: 14)-nucleic acid sequence of constant region (SEQ ID NO: 21) | Nucleic acid sequence of light chain (SEQ ID NO: 17)-linking sequence (SEQ ID NO: 22)-nucleic acid sequence of heavy chain (SEQ ID NO: 16)-nucleic acid sequence of constant region (SEQ ID NO: 21) |

(III) Construction of Chimeric Antibody and scFv-Fc Expression Vector

The Fc fragment constant region of heavy chain constant region (the nucleic acid sequence is shown in SEQ ID NO: 21) is cloned from human blood cells (Anhui Blood Center). Using DNA recombination technology and anchored PCR technology, the light chain, linking sequence ((GGCGGCGGCGGCAGC)$_3$, SEQ ID NO:22), heavy chain and Fc fragments are joined to form scFv-Fc fragments, and double enzyme cutting sites are introduced at both ends of scFv-Fc to clone a matched double enzyme digestion plasmid, that is, a scFv-Fc expression vector is obtained. The cloned DNA sequence is confirmed by sequencing. The cells of the subsequent experimental materials are transfected with this kind of plasmids, which are purified to obtain chimeric antibodies ChAb2 and ChAb1.

Test Example 1

(I) LunX Binding Activity of the Chimeric Antibody (ELISA)

The chimeric antibody constructed in Example 1 binds human LunX protein with high specificity and strength, and said LunX protein is the recombinant LunX protein described in Example 1. ELISA analysis is performed on the chimeric antibodies constructed in Example 1. The recombinant LunX protein is diluted to a concentration of 10 µg/ml with a coating buffer (0.1 M carbonate buffer, pH 9.6). A 96-well ELISA plate is coated, 100 µl/well, overnight at 4° C., washed 3 times with PBST (0.05% Tween 20-PBS, pH 7.4), blocked with 1% BSA, and incubated at 37° C. for 2 hours. The 96-well ELISA plate is washed 3 times with PBST, and is separately added with a double ratio-diluted the chimeric antibody, 4 gradients are set, IgG is used as a negative control, and PBS is used as a zero well, 100 µl/well, and incubated at 37° C. for 1 hour. The 96-well ELISA plate is washed 3 times with PBST, and each well is added with 100 µl of horseradish peroxidase (HRP)-labeled mouse anti-human IgG antibody (purchased from BOSTER Biological Technology co.ltd, 1:10000 dilution), and incubated at 37° C. for 1 hour. After washing, each well is added with 100 µl of TMB substrate solution, and keep the same in the dark for 10-15 minutes for color development. The stop solution (1M HCl) is added at 100 µl/well. After terminating the reaction, the assay is performed using a microplate reader. The absorbance at a wavelength of 450 nm (OD450) and absorbance at a wavelength of 630 nm (OD630) are read. Then $\Delta OD_{450} = OD_{450} - OD_{630}$ is calculated, and the results are shown in FIG. 1.

As shown in the ELISA results of FIG. 1, the chimeric antibodies ChAb2 and ChAb1 are able to specifically bind to the human LunX protein.

(II) Activity of Chimeric Antibodies Binding to LunX Protein on the Surface of Lung Cancer Cells (Flow Cytometry)

Figure 2:
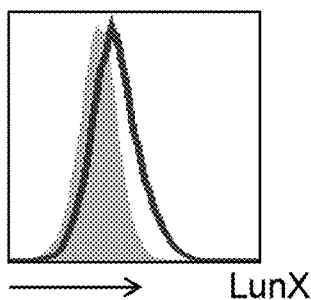
FIG. 2 shows the results of activity of a chimeric antibody in one embodiment of the present invention binding to LunX protein on the surface of the lung cancer cell.

Fresh lung cancer NCI-H292 cells (purchased from the Shanghai Cell Bank of the Chinese Academy of Sciences) are divided into two groups; one group is labeled with chimeric antibody and the other group is labeled with human IgG (control). Two groups are further labeled with FITC-labeled mouse anti-human IgG antibody against human IgG. All the labeling steps are performed at 4° C. for 30 minutes. The cells are collected by centrifugation at 350 g for 5 minutes, and washed 3 times with 1×PBS. The results of flow cytometry (BD FACS Calibur) are shown in FIG. 2. It can be seen that the chimeric antibody ChAb1 is capable of binding to the LunX protein on the surface of live lung cancer cells. Similarly, flow cytometry results show that the chimeric antibody ChAb2 is also able to bind to the LunX protein on the surface of live lung cancer cells.

(III) Antibody-Dependent Cell-Mediated Cytotoxicity (ADCC)

Figure 3:
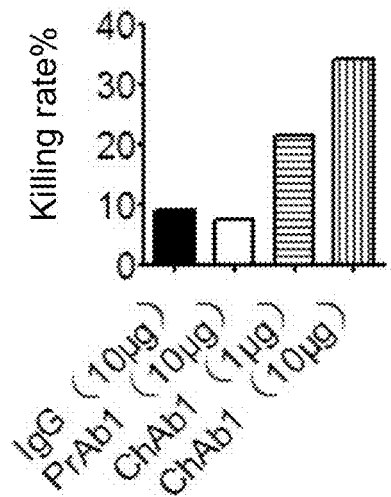
FIG. 3 shows the results of antibody-dependent cell-mediated cytotoxicity of chimeric antibodies detected by flow cytometry.

Lymphocytes are isolated from normal human peripheral blood by Ficoll (peripheral blood lymphocyte separation medium, Solarbio Company) centrifugation method at 380 g for 30 min, and resuspended in 1×PBS. Subsequently, NK cells are purified using a NK cell sorting kit (Miltenyi, Human NK Cell Isolation Kit). NK is used as an effector cell, NCI-H292 (Shanghai Cell Bank of the Chinese Academy of Sciences) lung cancer cells as used as target cells, co-incubation and killing experiments are performed at 37° C. for 4 h based on an effector-target ratio of 20:1. 10 µg of IgG, 10 µg of PrAb1, 1 µg of ChAb1, and 10 µg of ChAb1 are separately added into the co-incubation system, to investigate whether the chimeric antibody of the present invention mediates the killing effect of NK cells on tumor cells. As shown in FIG. 3, 7AAD is used to detect killed tumor cells, and the results show that the chimeric antibody ChAb1 is able to mediate ADCC effect and is dose-dependent. Similarly, cell-mediated cytotoxicity analysis shows that chimeric antibody ChAb2 can also mediate ADCC effect and is dose-dependent.

Figure 4:
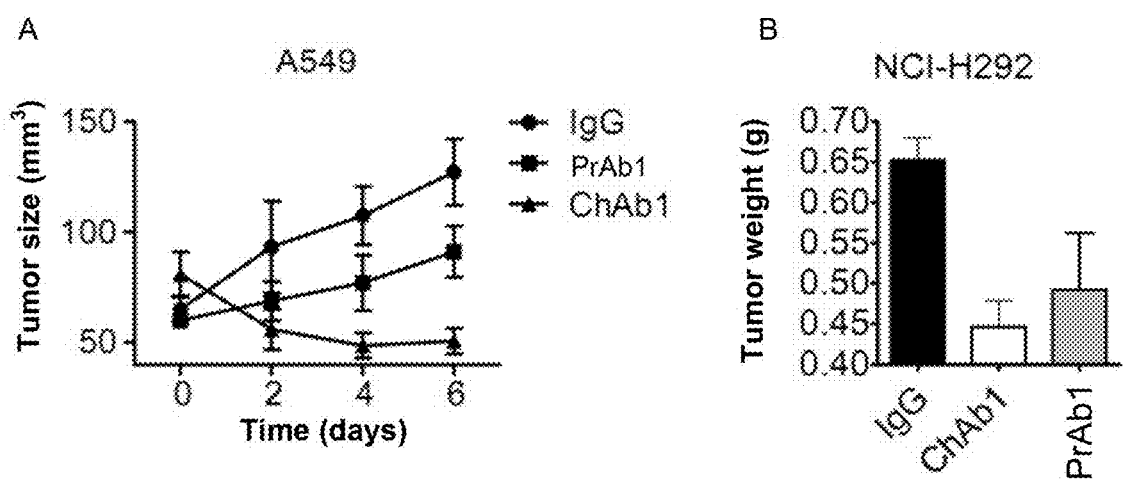
FIG. 4 shows the results of activity of a chimeric antibody in one embodiment of the present invention for inhibiting tumor growth in vivo.

(IV) Activity of the Chimeric Antibody in Inhibiting the Growth of Tumor In Vivo NCI-H292 and A549 cells (Shanghai Cell Bank of the Chinese Academy of Sciences) are amplified and cultured in vitro. The cells are collected and washed once with 1×PBS. Then the cells are collected by centrifugation at 800 rpm for 10 minutes, and resuspended in physiological saline at a concentration of 2×10$^7$ cells/ml. 200 µl of the cells are inoculated subcutaneously into the armpits of 6-7 weeks-old nude mice, and the total number of inoculated nude mice is 24. The mice inoculated with NCI-H292 and A549 cells are divided into two groups one week later, i.e. antibody group and IgG group; 6 mice in each group, and 20 mg/kg of antibody is tail vein injected every other day (20 mg antibody per kg mouse). After treating for 10 times, the long side and short side of the subcutaneous tumor are measured, and weighed the tumor. The tumor size can be detected according to an empirical formula (tumor size=long side× short side×short side/2), and the results are shown in FIG. 4 (wherein, FIG. 4A shows the tumor size measuring results of the mice inoculated with A549 cells, and FIG. 4B shows a tumor weight measuring results of mice inoculated with NCI-H292 cells). The results indicate that the chimeric antibody ChAb1 is capable of inhibiting tumor growth in vivo and has a stronger inhibitory activity than that of the originally obtained murine antibody PrAb1. Similarly, the results of activity assay in vivo show that the chimeric antibody ChAb2 also has an activity of inhibiting tumor growth in vivo.

From the results of the test example, it can be seen that the specificity and antitumor activity of the chimeric antibody obtained by the present invention are preferred.

While some preferred embodiments of the present invention are described above, the present invention is not limited to the details in those embodiments. Those skilled in the art can make simple modifications and variations to the technical scheme of the present invention, without departing from the spirit of the present invention. However, all these simple modifications and variations shall be deemed as falling into the scope of protection of the present invention.

In addition, it should be noted that the specific technical features described in above embodiments can be combined in any appropriate form, provided that there is no conflict. To avoid unnecessary repetition, the possible combinations are not described specifically in the present invention.

Moreover, different embodiments of the present invention can be combined freely as required, as long as the combinations don't deviate from the ideal and spirit of the present invention. However, such combinations shall also be deemed as falling into the scope disclosed in the present invention.

The invention claimed is:

1. An antibody or antibody fragment capable of binding to a lung-specific X protein, wherein the antibody or antibody fragment comprises heavy chain CDRs with amino acid sequences of SEQ ID NO: 1, SEQ ID NO: 2 and SEQ ID NO: 3 and light chain CDRs with amino acid sequences of SEQ ID NO: 4, SEQ ID NO: 5 and SEQ ID NO: 6;

or the antibody or antibody fragment comprises heavy chain CDRs with amino acid sequences of SEQ ID NO: 1, SEQ ID NO: 7 and SEQ ID NO: 3 and light chain CDRs with amino acid sequences of SEQ ID NO: 8, SEQ ID NO: 5 and SEQ ID NO: 6.

2. The antibody or antibody fragment according to claim 1, wherein the antibody or antibody fragment is capable of binding to the amino acid sequence shown in SEQ ID NO: 9.

3. The antibody or antibody fragment according to claim 1, wherein the amino acid sequence of the heavy chain variable region of the antibody or antibody fragment is shown in SEQ ID NO: 10 or SEQ ID NO: 12; and/or, the amino acid sequence of the light chain variable region of the antibody or antibody fragment is shown in SEQ ID NO: 11 or SEQ ID NO: 13.

4. The antibody or antibody fragment according to claim 1, wherein the antibody is a chimeric antibody or a humanized antibody.

5. A composition, containing the antibodies or antibody fragments according to claim 1 and pharmaceutically acceptable carriers.

6. A kit for detecting a lung-specific X protein in a sample, which includes the antibodies or antibody fragments according to claim 1.

7. A nucleic acid encoding the antibody or antibody fragment according to claim 1.

8. A recombinant vector or transformant containing the nucleic acid according to claim 7.

* * * * *